US009700705B2

(12) United States Patent
Lesch, Jr. et al.

(10) Patent No.: US 9,700,705 B2
(45) Date of Patent: *Jul. 11, 2017

(54) BALLOON CATHETER INFLATION APPARATUS AND METHODS

(71) Applicant: ENTELLUS MEDICAL, INC., Plymouth, MN (US)

(72) Inventors: Paul R. Lesch, Jr., Lino Lakes, MN (US); Paul A. Vajgrt, Saint Michael, MN (US); Timothy B. Petrick, Brooklyn Park, MN (US)

(73) Assignee: ENTELLUS MEDICAL, INC., Plymouth, MN (US)

( * ) Notice: Subject to any disclaimer, the term of this patent is extended or adjusted under 35 U.S.C. 154(b) by 66 days.

This patent is subject to a terminal disclaimer.

(21) Appl. No.: 14/796,948

(22) Filed: Jul. 10, 2015

(65) Prior Publication Data

US 2015/0352342 A1 Dec. 10, 2015

Related U.S. Application Data

(63) Continuation of application No. 12/372,691, filed on Feb. 17, 2009, now Pat. No. 9,101,739.

(51) Int. Cl.
*A61M 29/00* (2006.01)
*A61M 25/10* (2013.01)
(Continued)

(52) U.S. Cl.
CPC ....... *A61M 25/10182* (2013.11); *A61B 17/24* (2013.01); *A61M 25/1018* (2013.01);
(Continued)

(58) Field of Classification Search
CPC ........ A61M 25/1018; A61M 25/10184; A61M 25/10185; A61M 39/22; A61M 2039/2413; A61M 2039/242
See application file for complete search history.

(56) References Cited

U.S. PATENT DOCUMENTS 4,743,230 A 5/1988 Nordquest
4,838,864 A 6/1989 Peterson
(Continued)

FOREIGN PATENT DOCUMENTS

JP S56-9068 7/1982

OTHER PUBLICATIONS

Brochure, Proxis Embolic Protection System, St. Jude Medical, 2006 (2 pages).
(Continued)

*Primary Examiner* — Katherine Rodjom
(74) *Attorney, Agent, or Firm* — Vista IP Law Group LLP

(57) ABSTRACT

An inflation device includes a syringe body containing a bore. The bore holds a fluid that is used to inflate a separate device such as a dilation balloon. A plunger assembly slides within the syringe bore and contains a sealing member that forms a fluid tight seal with the syringe body. A shut-off valve is disposed within the distal end of the syringe body. The distal end of the syringe body has a fluid bypass channel fluidically coupled to the aperture of a connector. The shut-off valve has a spring-biased moveable piston with a bypass lumen contained therein, wherein the bypass lumen forms a fluid path between the bore and the fluid bypass channel when the pressure of the fluid is below a threshold value. The fluid path between the bore and the fluid bypass channel is interrupted when the pressure of the fluid is above the threshold value.

14 Claims, 11 Drawing Sheets

(51) Int. Cl.

| | | |
|---|---|---|
| *A61M 39/12* | (2006.01) | |
| *A61M 29/02* | (2006.01) | |
| *A61M 39/22* | (2006.01) | |
| *A61B 17/24* | (2006.01) | |
| *A61M 39/10* | (2006.01) | |

(52) U.S. Cl.
CPC ...... *A61M 25/10185* (2013.11); *A61M 25/10187* (2013.11); *A61M 29/02* (2013.01); *A61M 39/12* (2013.01); *A61M 39/22* (2013.01); *A61M 2039/1033* (2013.01); *A61M 2210/0618* (2013.01)

(56) References Cited

U.S. PATENT DOCUMENTS

| | | | |
|---|---|---|---|
| 5,279,582 A | 1/1994 | Davison et al. | |
| 5,997,512 A | 12/1999 | Shaw | |
| 6,050,973 A | 4/2000 | Duffy | |
| 7,520,876 B2 | 4/2009 | Ressemann et al. | |
| 7,678,099 B2 | 3/2010 | Ressemann et al. | |
| 7,842,062 B2 | 11/2010 | Keith et al. | |
| 7,879,061 B2 | 2/2011 | Keith et al. | |
| 7,918,871 B2 | 4/2011 | Truitt et al. | |
| 8,241,266 B2 | 8/2012 | Keith et al. | |
| 8,277,478 B2 | 10/2012 | Drontle et al. | |
| 8,282,667 B2 | 10/2012 | Drontle et al. | |
| 8,348,969 B2 | 1/2013 | Keith et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 8,657,846 B2 | 2/2014 | Keith et al. | |
| 8,801,670 B2 | 8/2014 | Drontle et al. | |
| 8,834,513 B2 | 9/2014 | Hanson et al. | |
| 8,882,795 B2 | 11/2014 | Drontle et al. | |
| 8,888,686 B2 | 11/2014 | Drontle et al. | |
| 8,915,938 B2 | 12/2014 | Keith et al. | |
| 8,986,340 B2 | 3/2015 | Drontle et al. | |
| 9,005,284 B2 | 4/2015 | Ressemann | |
| 2004/0098017 A1 | 5/2004 | Saab et al. | |
| 2007/0010787 A1 | 1/2007 | Hackett et al. | |
| 2008/0015472 A1 | 1/2008 | Ressemann et al. | |
| 2008/0172033 A1 | 7/2008 | Keith et al. | |
| 2010/0274222 A1 | 10/2010 | Setliff, III et al. | |
| 2012/0283625 A1 | 11/2012 | Keith et al. | |
| 2013/0030458 A1 | 1/2013 | Drontle et al. | |
| 2013/0072958 A1 | 3/2013 | Ressemann et al. | |
| 2013/0123833 A1 | 5/2013 | Lesch et al. | |
| 2014/0350520 A1 | 11/2014 | Drontle et al. | |
| 2014/0357959 A1 | 12/2014 | Hanson et al. | |
| 2014/0364700 A1 | 12/2014 | Hanson et al. | |
| 2014/0378776 A1 | 12/2014 | Hanson et al. | |
| 2015/0031950 A1 | 1/2015 | Drontle et al. | |
| 2015/0045827 A1 | 2/2015 | Drontle et al. | |
| 2015/0105818 A1 | 4/2015 | Keith et al. | |

OTHER PUBLICATIONS

Inflation Device, Braun Sharing Expertise, http//www.bbraunusa.com/index.cfm?uuid=5778152AD0B759A1E38E4978386E21BD, Feb. 23, 2009 (1 page).

Iro, H., J. Zenk. "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).

PCT International Search Report for PCT/US2010/023479, Applicant: Entellus Medical, Inc., Form PCT/ISA/210 and 220, dated Apr. 13, 2010 (4 page).

PCT Written Opinion of the International Search Authority for PCT/US2010/023479, Applicant: Entellus Medical, Inc., Form PCT/ISA/237, dated Apr. 13, 2010 (6 pages).

PCT International Preliminary Report on Patentability (Chapter I of the Patent Cooperation Treaty) in International Application No. PCT/US2010/023479 dated Sep. 1, 2011 (8 pages).

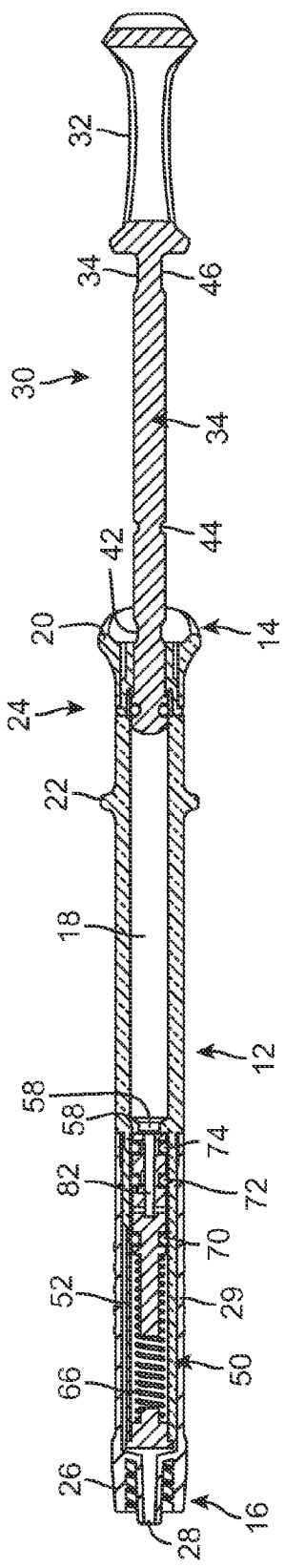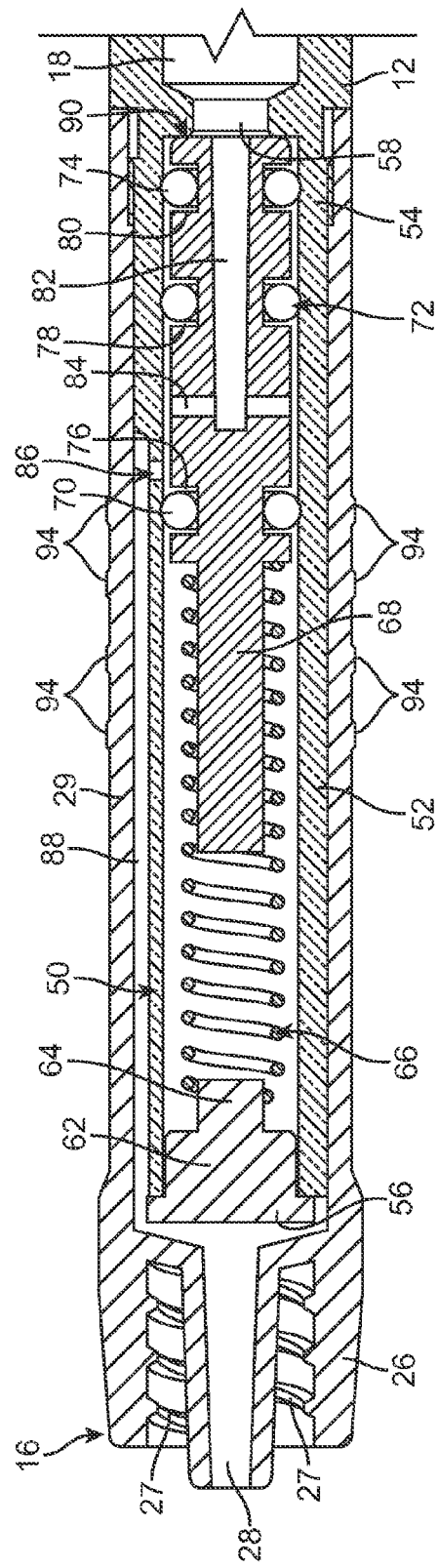
FIG. 7
FIG. 8

BALLOON CATHETER INFLATION APPARATUS AND METHODS

RELATED APPLICATION DATA

This Application is a continuation of U.S. patent application Ser. No. 12/372,691 filed on Feb. 17, 2009, now issued as U.S. Pat. No. 9,101,739. Priority is claimed pursuant to 35 U.S.C. §120. The above-noted Patent Application is incorporated by reference as if set forth fully herein.

FIELD OF THE INVENTION

The field of the invention generally relates to balloon inflation devices and methods. Balloon inflation devices are typically used in constricted spaces within the human or mammalian body. Balloon dilation has become popular in numerous medical fields of application. One particular use of balloon dilation is the treatment of sinusitis.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has an opening into the nasal passage called an ostium. When the mucosa of one or more of the ostia or regions near the ostia become inflamed, the egress of mucous is interrupted, setting the stage for an infection and/or inflammation of the sinus cavity, i.e., sinusitis. Infection/inflammations of the maxillary with or without the ethmoid sinuses make up the vast majority of cases of sinusitis, with far fewer cases involving the sphenoids and frontals. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter (a balloon catheter). Generally, the inflatable balloon is inserted into the constricted sinus passageway in a deflated state. The balloon is then expanded to open or reduce the degree of constriction in the sinus passageway being treated. A variety of devices (inflation devices) have been used to inflate and deflate the inflatable balloon located on the catheters. Many of these devices used in these treatments have been bulky and cumbersome to use. Often an assistant to the physician is utilized to perform the inflating/deflating of the balloon catheter, as the overall systems include multiple components necessitating multiple operators working in conjunction with one another.

Existing inflation devices typically include a rather large volume syringe having a barrel that is filled with an incompressible fluid such as saline. The syringe includes a plunger assembly having a shaft portion that terminates at one end with a sealing member located within the syringe barrel. The sealing member is sealed (or acts as a seal) within the interior of the bore. The other end of the stem is typically secured to a depressor or the like that enables the user to actuate the syringe. The inflation devices also typically include a pressure gauge. The pressure gauge measures, indirectly, the pressure within the inflatable balloon. Pressure to the inflatable balloon is adjusted by the degree of insertion of the plunger assembly within the barrel of the syringe. The pressure is indicated by the pressure gauge, and the user can adjust the pressure accordingly by relative movement of the plunger with the syringe barrel. A syringe having a large volume (and thus is large and bulky) is typically chosen to provide for adequate vacuum pressures that overcome the volume compliance of the pressure gauge, and to a lesser extent the volume compliance of the remainder of the closed system including the balloon dilation catheter itself. As a result, existing inflation devices are bulky and cumbersome to work with, requiring a dedicated operator just for its operation. Thus, medical interventional procedures that require use of balloon dilation may require additional personnel to operate the balloon inflation device in addition to other interventional devices.

There thus is a need for an inflation device that would simplify the dilation of an expandable member such as a dilation balloon. Such a device should be more compact than existing inflation devices and enable a single user to operate the inflation device during inflation/deflation. Such a device and any system that would incorporate the device would be particularly useful and advantageous in procedures where the dilation balloon is used to dilate constricted spaces, particularly constricted spaces in the sinus cavities.

SUMMARY OF THE INVENTION

In a first embodiment of the invention, an inflation device includes a syringe body having proximal end and a distal end and a bore contained therein, the bore configured to hold a fluid therein. The inflation device includes a plunger assembly comprising a shaft having a proximal end and a distal end, the proximal end of the shaft operatively coupled to an actuator, the distal end of the plunger assembly comprising a sealing member configured to form a fluid tight seal with the syringe body. A connector is disposed at the distal end of the inflation device, the connector containing an aperture configured for passage of fluid. The inflation device includes a shut-off valve disposed within a valve body, the shut-off valve in fluid communication with the syringe body, the valve body including an aperture therein that communicates with an outlet channel external to valve body that is fluidically connected to the aperture of the connector. The shut-off valve has a spring-biased moveable piston having a bypass lumen contained therein, wherein the bypass lumen forms a fluid path between the bore and the outlet channel when the pressure of the fluid is below a threshold value and wherein the fluid path between the bore and the outlet channel is interrupted when the pressure of the fluid is above the threshold value.

In a second embodiment of the invention, a system for dilating a natural sinus ostium includes a balloon dilation catheter having an elongate member having a dilation balloon at one end and a first connector at an opposing end. The system further includes an inflation device with a syringe body having proximal end and a distal end and a bore contained therein, the bore configured to hold a fluid therein. The inflation device includes a plunger assembly configured for slidable movement within the syringe bore, the plunger assembly comprising a shaft having a sealing member configured to form a fluid tight seal with the syringe body. A second connector is disposed at the distal end of the inflation device, the second connector containing an aperture configured for passage of fluid, the second connector configured to mate with the first connector of the balloon dilation catheter. A fluid bypass channel is disposed in the distal end of the syringe body and fluidically coupled to the aperture of the second connector. The inflation device includes a shut-off valve made from a spring-biased moveable piston having a bypass lumen contained therein, wherein the bypass lumen forms a fluid path between the bore and the fluid bypass channel in the syringe body when the pressure of the fluid is below a threshold value and wherein the fluid path between the bore and the fluid bypass channel is interrupted when the pressure of the fluid is above the threshold value.

In another embodiment of the invention, a system for dilating a restricted part of the human anatomy includes a balloon dilation catheter and an inflation device. The inflation device is configured for fluidic attachment to the balloon dilation catheter, the inflation device has a syringe body having proximal end and a distal end and a bore contained therein, the bore configured to hold a fluid therein. The inflation device also has a plunger assembly comprising a shaft having a proximal end and a distal end, wherein the proximal end of the shaft is operatively coupled to an actuator and the distal end of the plunger assembly has a sealing member configured to form a fluid tight seal with the syringe body. A connector is disposed at the distal end of the inflation device, the connector containing an aperture configured for passage of fluid. The inflation device includes a shut-off valve disposed within a valve body, the shut-off valve in fluid communication with the syringe body. The valve body includes an aperture therein that communicates with an outlet channel external to valve body that is fluidically connected to the aperture of the connector, the shut-off valve having a spring-biased moveable piston having a bypass lumen contained therein, wherein the bypass lumen forms a fluid path between the bore and the outlet channel when the pressure of the fluid is below a threshold value and wherein the fluid path between the bore and the outlet channel is interrupted when the pressure of the fluid is above the threshold value.

BRIEF DESCRIPTION OF THE DRAWINGS

FIG. 1 illustrates a plunger assembly that is fully inserted into the bore of a syringe body.

FIG. 2 illustrates the plunger assembly partially retracted in the proximal direction from the bore of the syringe body.

FIG. 7 is a cross-sectional view of the inflation device illustrating the plunger assembly being withdrawn proximally. Proximal retraction of the plunger assembly is employed to deflate the inflatable balloon.

FIG. 8 is an enlarged, cross-sectional view of the distal end of the inflation device. The moveable piston of the shut-off valve is illustrated abutting a proximal stop within the interior of the syringe body. The proximal stop prevents unwanted or excess movement of the moveable piston when the plunger assembly is withdrawn in the proximal direction to deflate the inflation balloon.

DETAILED DESCRIPTION OF THE ILLUSTRATED EMBODIMENTS

Figure 1:
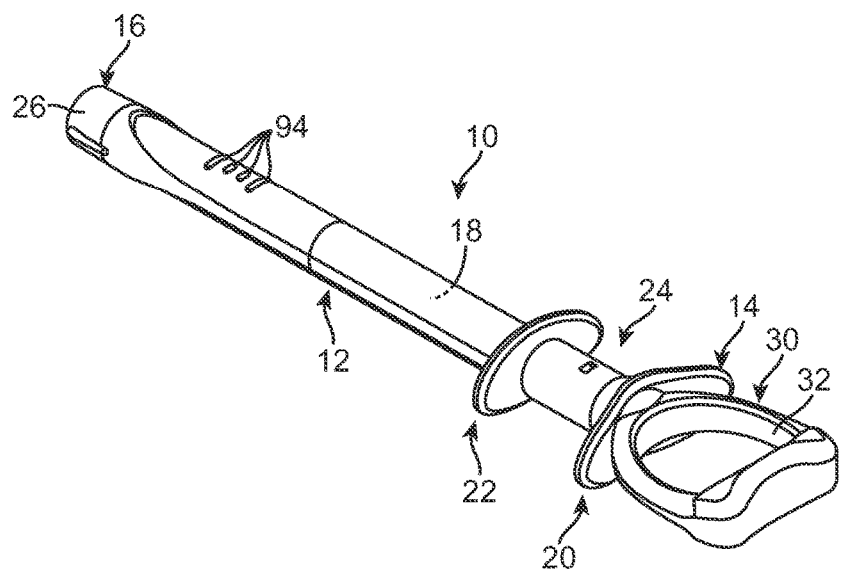
FIG. 1 illustrates a perspective view of an inflation device according to one embodiment.
Figure 2:
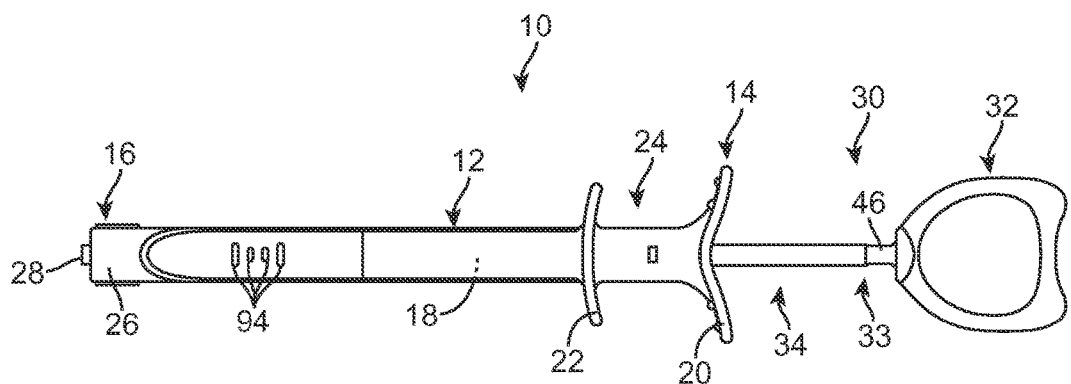
FIG. 2 is a plan view of the inflation device of FIG. 1.

FIGS. 1 and 2 illustrate a inflation device 10 that is used to dilate or inflate an expandable member such as a dilation balloon 100 (illustrated in FIGS. 10-12) that is disposed on a distal end of an elongate member 102 (also illustrated in FIGS. 10-12) such as a balloon catheter 104. The inflation device 10 is configured as an actuator that is used to selectively push or pull a substantially incompressible fluid into or out of the dilation balloon 100. The inflation device 10 may take the form of a syringe or the like. For example, in the embodiment illustrated in FIGS. 1 and 2, the inflation device 10 includes a syringe body 12 that includes a proximal end 14, a distal end 16, and a central bore 18 (better seen in FIGS. 3-5, 6A, 6B, and 7-9). The syringe body 12 is typically made from a polymer material such as polycarbonate or other plastic-based materials although a variety of materials may be used. The shape of the syringe body 12 is typically cylindrical although the invention is not limited to any particular geometrical shape. The central bore 18 defines an internal volume of the syringe body 12 that is configured to hold a fluid such as saline. The total available internal volume of the syringe body 12 may vary but typically is within the range of 0 mL to about 2.2 mL. Not all of this total available volume may be used, however. For example, actual volume of fluid contained in the syringe body 12 after priming may be in the range of about 1.5 mL to about 2.0 mL. The length of the syringe body 12 may also vary but typically the central bore 18 portion is within the range of about 2.5 inches to about 3 inches.

The proximal end 14 of the syringe body 12 may include one or more optional flanges 20, 22 disposed about the periphery of the syringe body 12. The flanges 20, 22 may be formed as circular or elliptical-shaped aprons that define a recess 24 that may be used to place one or more fingers during operation of the inflation device 10. For example, the recess 24 formed between the proximal flange 20 and the distal flange 22 may be used by the physician or other user to place his or her forefinger (or other/additional finger(s)) during actuation of the inflation device 10. The exact shape and dimensions of the flanges 20, 22 may be tailored to ensure a comfortable, ergonomic fit with the user's hands.

Still referring to FIGS. 1 and 2, the distal end 16 of the syringe body 12 includes a connector 26. The connector 26 may be affixed to the syringe body 12 as a separate structure or, alternatively, the connector 26 may be integrally formed with the syringe body 12 (e.g., molded as part of syringe body 12). For example, the connector 26 may include a housing 29 that extends proximally and is bonded to or otherwise secured to the syringe body 12. The connector 26 includes an aperture 28 (best seen in FIG. 2 and later FIGS) that, except during actuation of a shut-off valve 50 described in more detail below, is in fluidic communication with the with the central bore 18 of the syringe body 12. In this regard, fluid is able to pass through the connector 26 as the inflation device 10 is actuated. The connector 26 may include any number of connectors typically used to connect medical components to one another. One such connector 26 is a Luer connector which is illustrated in FIGS. 1-5, 6A, 6B, 7, 8, and 10-12. Luer connector 26 has a threaded portion 27 that is configured to engage with a mating interface or connector. Other such connectors 26 are, however, contemplated to fall within the scope of the invention.

The inflation device 10 further includes a plunger assembly 30 that is dimensioned for insertion into the bore 18 of the syringe body 12. The plunger assembly 30 includes an actuator 32 that is coupled to a proximal end 33 of shaft 34. The actuator 32 may be formed as a ring or the like as illustrated in FIGS. 1 and 2. In this regard, the ring is dimensioned to that the physician's (or other user's) thumb may be inserted within the ring. Movement of the actuator 32 in the proximal direction will remove the shaft 34 from the bore 18 of the syringe body 12. Conversely, movement of the actuator 32 in the distal direction will advance the shaft 34 into the bore 18 of the syringe body 12.

Figure 3:
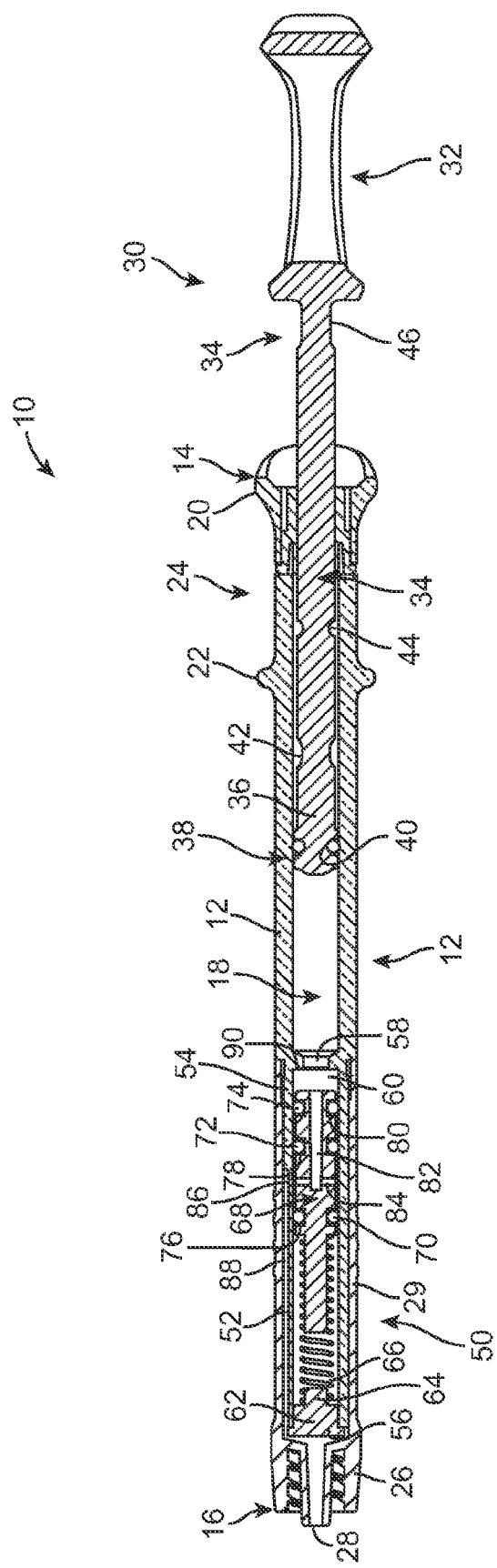
FIG. 3 is a cross-sectional view of the inflation device illustrated in FIG. 2. A shut-off valve is illustrated in the distal portion of the syringe body.

Turning now to FIG. 3, the shaft 34 is an elongate structure that is dimensioned to fit within the bore 18 of the syringe body 12. The distal end 36 of the shaft 34 includes a sealing member 38 that forms a fluidic seal between the shaft 34 and the internal surface of the syringe body 12 defined by the bore 18. As seen in FIG. 3, the sealing member 38 may be formed from an o-ring that is located in a recess 40 located at the distal end 36 of the shaft 34. The shaft 34 may optionally incorporate one or more detents 42, 44, 46 located at different locations along the shaft 34. For example, there may be a distal detent 42, an intermediate detent 44, and a proximal detent 46. As explained in more detail below, in certain embodiments, the detents 42, 44, 46 may provide tactile and/or audible feedback to the user to facilitate the prepping and use of the inflation device 10.

Figure 4:
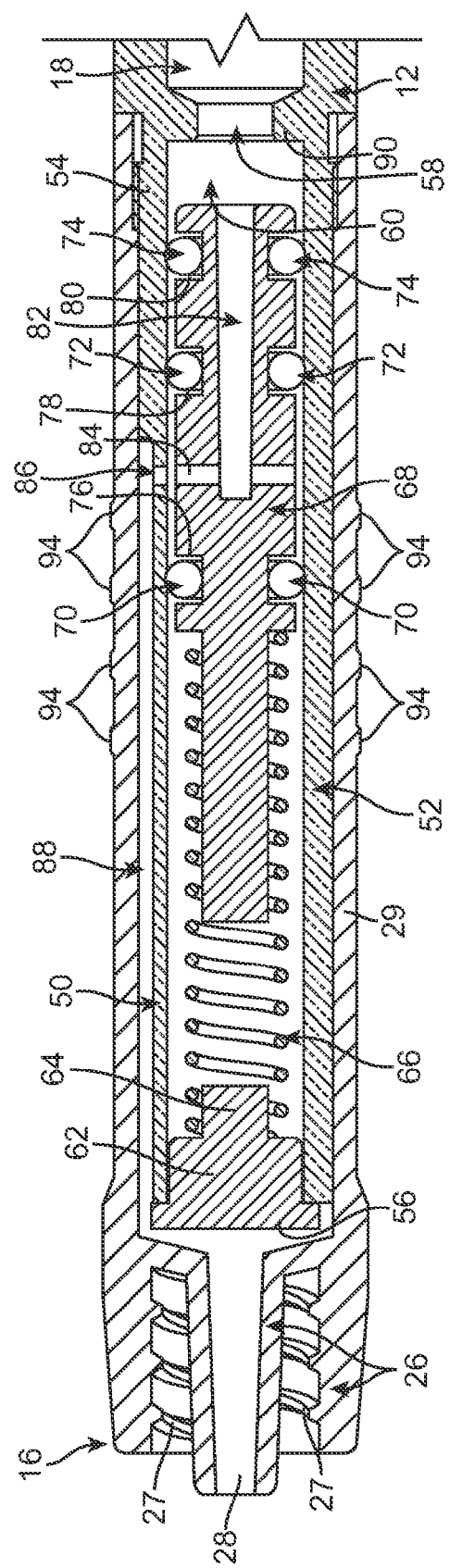
FIG. 4 is an enlarged, cross-sectional view of the distal end of the inflation device illustrated in FIG. 3.
Figure 5:
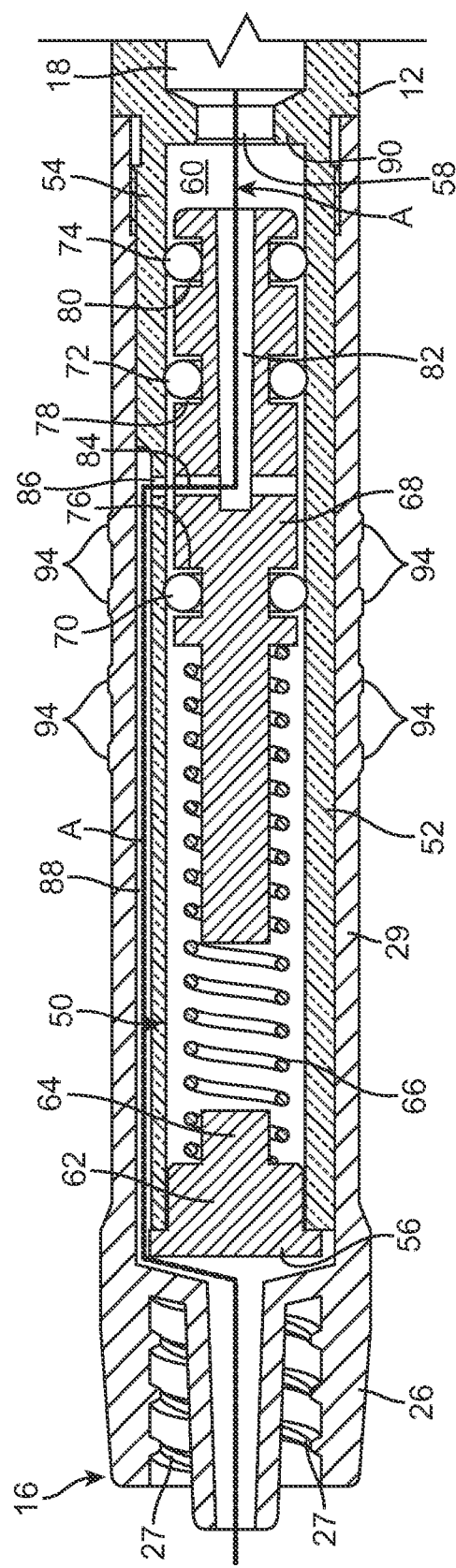
FIG. 5 is an enlarged, cross-sectional view of the distal end of the inflation device illustrated in FIG. 3 with the addition of a dashed line illustrating the flow path of a fluid used in conjunction with the balloon inflation device. In this configuration, the inflation fluid exits the valve body and passes through an outer channel that is in fluid communication with an outlet of the syringe body.

Referring now to FIGS. 3 and 4, a shut-off valve 50 is located at the distal end 16 of the syringe body 12. The shut-off valve 50 is designed to permit passage of fluid (e.g., saline) from the bore 18 of the syringe body 12 and out the aperture 28 of the connector 26 up to a threshold or pre-set pressure level. Once the threshold or pre-set pressure level has been exceeded, the design of the shut-off valve limits additional fluid from exiting the inflation device 10.

The shut-off valve 50 is located within a valve body 52 or housing contained at the distal end 16 of the syringe body 12. The valve body 52 may be integrally formed with the syringe body 12 or, alternatively, the valve body 52 may be a separate structure that is bonded, welded, or molded together with the syringe body 12. For instance, the shut-off valve 50 may be physically separate from the syringe body 12 and attached via a piece of tubing or similar conduit. The shut-off valve 50 may be disposed outside or external to the syringe body 12. The valve body 52 includes a proximal end 54 and a distal end 56. The proximal end 54 of the valve body 52 includes an inlet aperture 58 that fluidically communicates with the bore 18 of the syringe body 12 and enables fluid to enter the valve space 60. The distal end 56 of the valve body 52 includes an end cap 62. The end cap 62 includes a mount 64 or the like for receiving one end of a compression spring 66. The opposing end of the compression spring 66 is mounted on a moveable piston 68.

As explained in more detail below, the moveable piston 68 moves distally and proximally within the valve space 60 as the plunger assembly 30 is advanced or retracted within the bore 18 of the syringe body 12. The moveable piston 68 includes a distal sealing member 70, an intermediate sealing member 72, and a proximal sealing member 74. In one aspect, the sealing members 70, 72, and 74 may include o-rings 70, 72, and 74 as currently illustrated in the drawings. The various o-rings 70, 72, 74 are mounted about the moveable piston 68 in respective grooves 76, 78, and 80. The o-rings 70, 72, 74 create a fluidic seal between the external surface of the moveable piston 68 and the interior surface of the valve body 52. As best seen in FIG. 4, the moveable piston 68 contains a bypass lumen 82 that communicates at one end with the valve space 60 and terminates at an outlet 84 located on the side of the moveable piston 68.

As best seen in FIG. 4, an aperture 86 is located in the valve body 52 and depending on the position of the moveable piston 68, is fluidically connected to the fluid contained in the bypass lumen 82. The aperture 86 located in the valve body 52 opens to an outlet channel 88 that is formed between the exterior surface of the valve body 52 and the housing 29. The outlet channel 88 fluidically communicates with the aperture 28 of the connector 26. In the orientation seen in FIG. 4, a fluid such as saline is able to enter the valve space 60 via the inlet aperture 58. As pressure is applied to the fluid by the plunger assembly 30, the fluid passes into the bypass lumen 82 and then through the aperture 86 into the outlet channel 88. The fluid can then continue through the outlet channel 88 and out the aperture 28 of the connector 26. The fluid would continue along the elongate member 102 and into the dilation balloon 100 (illustrated in FIGS. 10-12).

In the configuration of FIG. 4, the aperture 86 of the valve body 52 is illustrated as being straddled by the distal o-ring 70 and the intermediate o-ring 72. In this configuration, a flow path is established between the bore 18 and the aperture 28 of the connector 26. The flow path is illustrated in dashed line A in FIG. 5. The position of the shut-off valve 50 illustrated in FIGS. 4 and 5 reflects a "neutral" position, which is a condition wherein the fluid pressure within the bore 18 of the syringe body 12 is lower than the pressure required to activate the shut-off valve 50. In this neutral position, fluid is able to exit the inflation device 10 and enter the elongate member 102 and dilation balloon 100 (illustrated in FIGS. 10-12). It should also be noted that, in one alternative embodiment, the distal o-ring 70 may be optional. Having a distal o-ring 70 does, however, prevent fluid from entering the space within the shut-off valve 50 occupied by the compression spring 66.

Figure 6A:
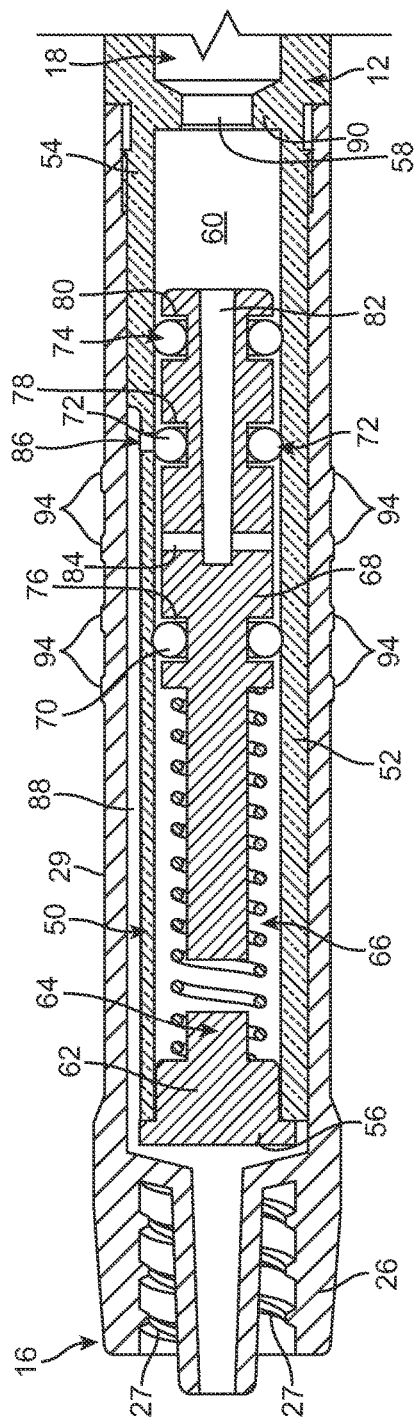
FIG. 6A is enlarged, cross-sectional view of the distal end of the inflation device illustrating an intermediate sealing member directly blocking an outlet aperture in the valve body of the shut-off valve. In this position, fluid is prevented from exiting the valve body.

As described herein, the piston 68 is moveable within the valve space 60. As the pressure of the fluid within the bore 18 is increased (by advancing the actuator 32 and shaft 34 distally), additional fluid is forced into the valve space 60. This forces the moveable piston 68 to slide distally and results in compression of the compression spring 66. The compression spring 66 will absorb this motion by compressing a commensurate amount to the pressure that is applied to the piston 68. As the pressure is increased to higher and higher values, the piston 68 is moved further distally until such point where the intermediate o-ring 72 covers or blocks the aperture 86. This state is illustrated in FIG. 6A. Once the aperture 86 is covered or otherwise blocked by the intermediate o-ring 72, the fluid communication path A to the aperture 28 of the connector 26 (and dilation balloon 100) is interrupted. This interruption of the flow path A prevents higher pressures within the bore 18 from being transferred to the dilation balloon 100. If a user applies additional pressure by depressing the plunger assembly 30 further within the syringe body 12, the moveable piston 68 will continue to advance distally. This state is illustrated in FIG. 6B.

Even though the intermediate o-ring 72 has moved distally with respect to the aperture 86, fluid flow is prevented from reaching the aperture 86 and outlet channel 88 because of the proximal o-ring 74. So long as the intermediate o-ring 72 and the proximal o-ring 74 straddle the aperture 86, fluid communication between the bore 18 and the attached elongate member 102 (e.g., balloon catheter 104) is interrupted.

Figure 6B:
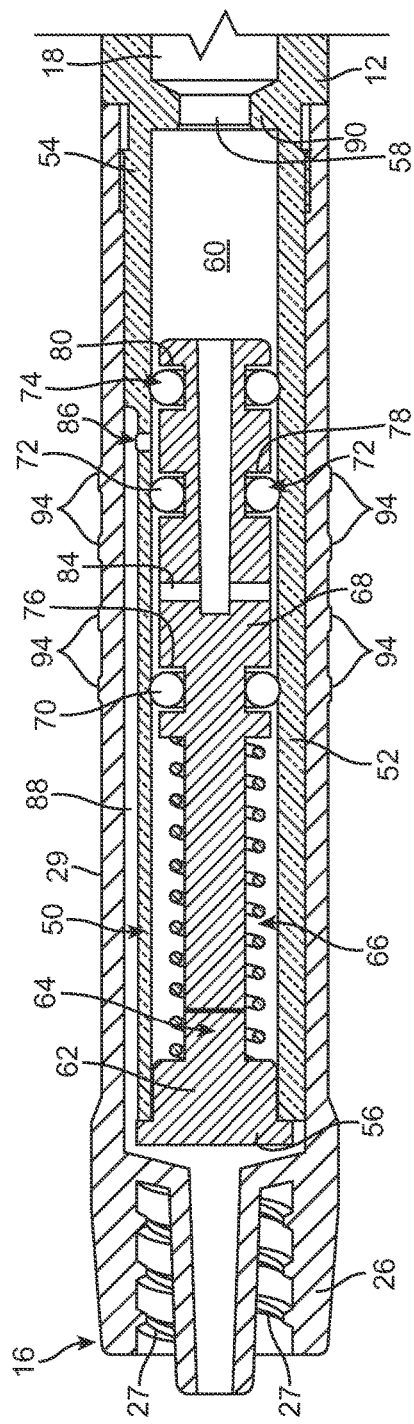
FIG. 6B is enlarged, cross-sectional view of the distal end of the inflation device illustrating the intermediate sealing member moving distally with respect to the outlet aperture in the valve body of the shut-off valve. This state may reflect additional pressure being applied to the plunger assembly as compared to the pressure applied in FIG. 6A. The outlet aperture is straddled by the intermediate sealing member and the proximal sealing member. Even in this position, fluid is prevented from exiting the valve body because of the straddling sealing members.

FIG. 6B illustrates the configuration of the pressure shut-off valve 50 at the condition where the pressure within the syringe body 12 (e.g., bore 18) is above the pre-specified pressure threshold which activates the shut-off valve 50. The moveable piston 68 has been advanced distally, until the piston 68 has fully compressed the spring 66. Alternatively (or additionally), the moveable piston 68 has advanced against the spring mount 64 of the end cap 62. The spring mount 64 thus acts as a stop for the piston 68. The compressed spring 66 and/or the spring mount 64 further limits distal advancement of the piston 68, regardless of how high the pressure in the bore 18 of the syringe body 12. In the position illustrated in FIG. 6B, the intermediate o-ring 72 and the proximal o-ring 74 interrupt the fluid path A to the balloon catheter 104, thus maintaining the pressure delivered to the balloon catheter 104 at the desired pre-set value. Therefore, the pressure applied to the dilation balloon 100 is limited by whatever pressure is required to compress the compression spring 66 to the point at which the fluid flow path A is interrupted by the intermediate o-ring 72 located on the moveable piston 68.

When it is desired to deflate the balloon catheter 104, the plunger assembly 30 is withdrawn proximally, as shown in FIG. 7. As the actuator 32 and shaft 34 are withdrawn proximally from the syringe body 12, the moveable piston 68 will also move in the proximal direction in response to the resultant decrease in pressure. When the moveable piston 68 achieves the "neutral" position, such as that illustrated in FIG. 4, fluid communication to the dilation balloon 100 is re-established, thereby allowing the fluid in the balloon catheter 104 to be withdrawn from the dilation balloon 100 into the bore 18 of the syringe body 12. Preferably a proximal stop 90 (illustrated in FIG. 8) prevents excessive movement of the piston 68 proximally such that under any negative pressure, fluid communication to the balloon catheter 104 remains open. The proximal stop 90 is an abutment that contacts the proximal end 54 of the moveable piston 68.

The desired maximum pressure that the balloon is exposed to can be "designed" into the shut-off valve 50 by varying one or more variables of components of the shut-off valve 50, as would be known to those skilled in the art. For example, a "stiffer" vs. "softer" compression spring 66 will result in a higher pressure require to shut off the valve. Alternatively, design variables associated with the amount of travel of the piston (shut-off "activation") can be considered. For a given compression spring 66, a shorter vs. longer distance from the "neutral" position to a "stopped" position determined by the position of the distal stop 64 (and associated position of the outlet) will alter the pressure required to activate the shut-off valve 50. For example, if the stop 64 is positioned (and associated variables such as position of the outlet aperture are positioned) to effectively shorten the amount of compression required to close the outlet, the resultant "activation pressure" pressure for shutting off the shut-off valve 50 will be lower. The diameter of the piston 68 (and associated components such as the o-ring seals and piston lumen) will also impact the pressure at which the shut-off valve 50 interrupts fluid communication. All other things being equal, a larger diameter piston 68 will result in a lower pressure required for shut-off.

Figure 9:
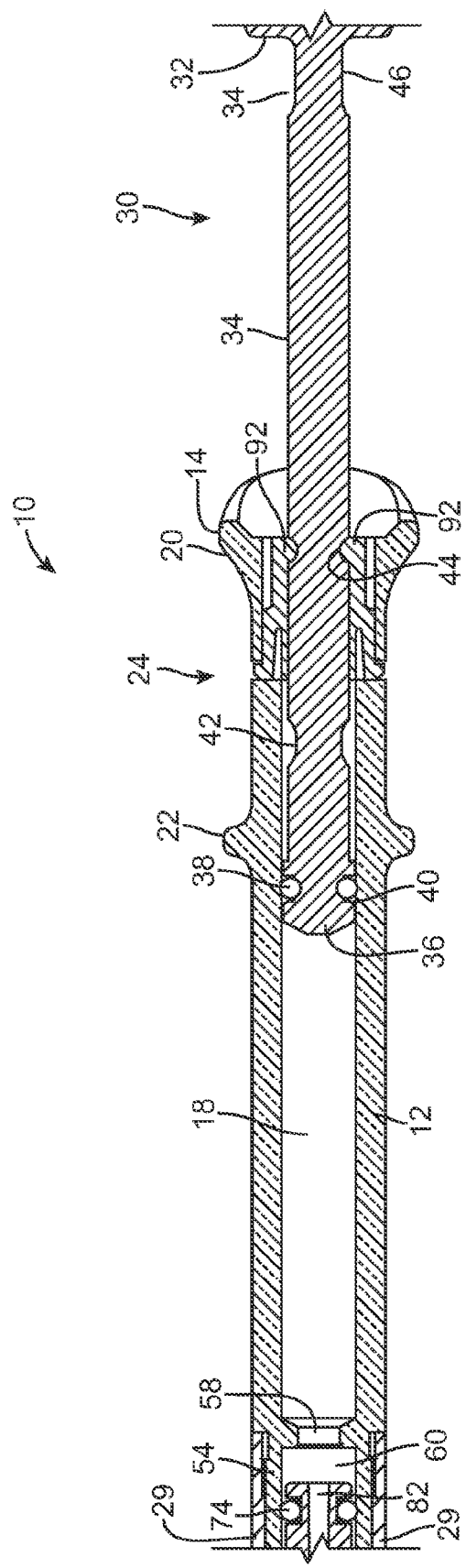
FIG. 9 illustrates a cross-sectional view of a portion of the proximal end of the inflation device. The shaft of the plunger assembly is illustrated with a plurality of detents disposed longitudinally along the length of the shaft. A projection or flange on the syringe body interfaces with the detents to provide tactile and/or audible feedback regarding the position of the shaft within the bore of the syringe body. The interface between the detents and the projection or flange may also act as a temporary lock between the syringe body and the plunger assembly.

Referring now to FIG. 9, in one embodiment, the shaft 34 of the plunger assembly 30 incorporates one or more detents 42, 44, 46 that operate in cooperation with a projection 92 located at the proximal end 14 of the syringe body 12. The projection 92 may include a ring, lip or bump that circumferentially or intermittently circumscribes the entrance to the bore 18 of the syringe body 12. As seen in FIG. 3, there are three circumferential detents about the shaft 34 including a distal detent 42, an intermediate detent 44, and a distal detent 46. The size and flexibility of the projection 92 is dimensioned to nest within the respective detents 42, 44, 46 as the shaft is moved axially within the syringe body 12. The detents 42, 44, 46 provide tactile and/or audible feedback to the user to facilitate prepping and use of the inflation apparatus during a dilation procedure. For example, the shaft 34 may "click" into place as the user advances or retracts the shaft 34 within the bore 18 of the syringe body 12. The "click" may be felt and/or heard by the user.

Figure 12:
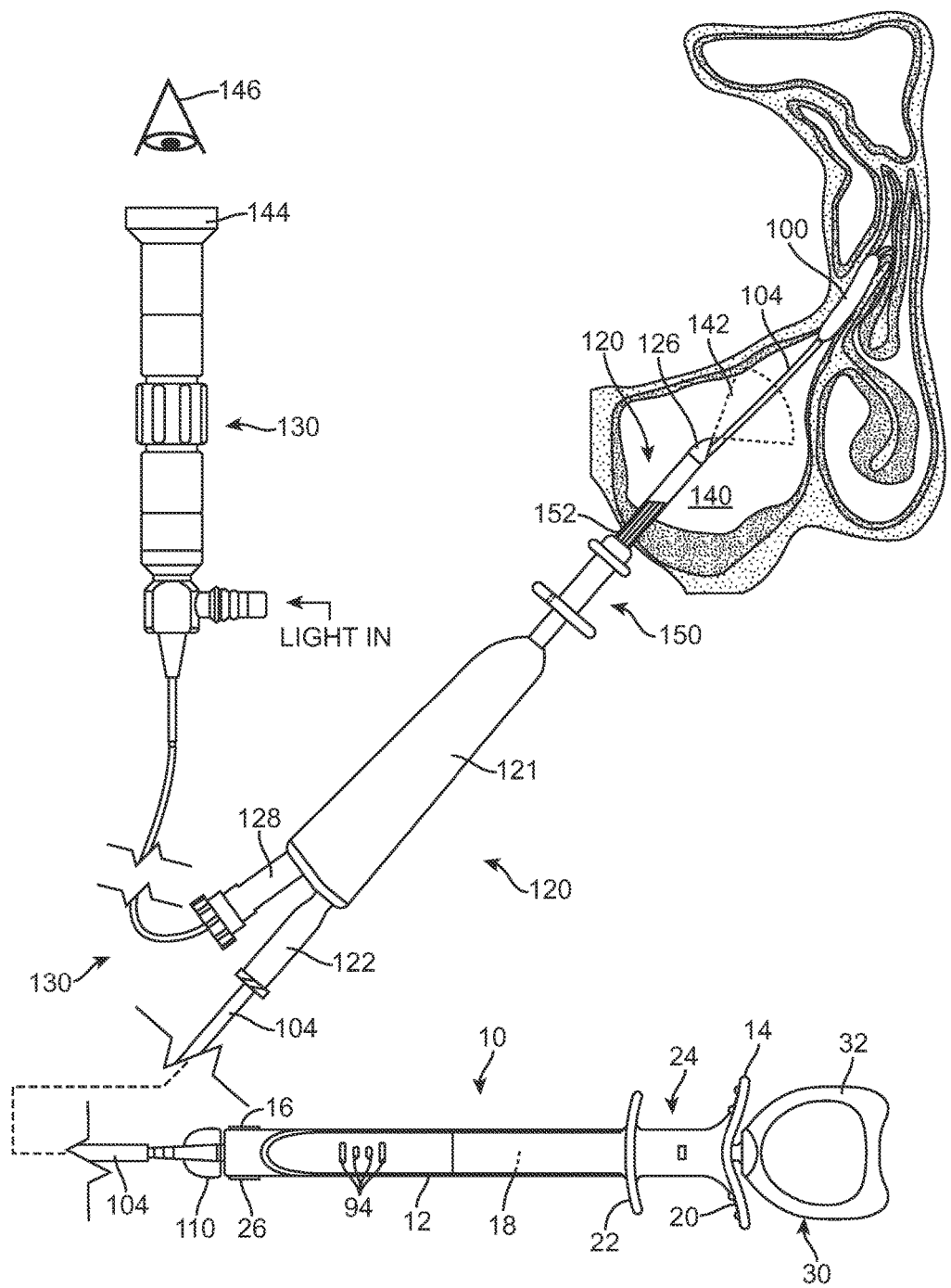
FIG. 12 illustrates a system incorporating the inflation device described herein. The system is used to access and treat the natural maxillary sinus ostium.

The proximal detent 46 is located adjacent to the actuator 32 and interfaces with the projection 92 when the plunger assembly 30 is completely advanced in the distal direction (e.g., as seen in FIGS. 1 and 12). This configuration is preferably how the inflation device 10 is stored prior to use. In this position, the projection 92 is maintained in a relaxed or "unflexed" condition, free from potential creeping.

To prep the inflation device 10, the connector 26 (with no balloon catheter 104 attached) is placed in saline or other inflation fluid. The plunger assembly 30 is then fully withdrawn in the proximal direction by proximal movement of the actuator 32. The shaft 34 is withdrawn proximally such that the intermediate detent 44 passes the projection and the distal detent 46 engages with the projection 92. Residual air may be present in the bore 18 of the syringe body 12 together with the fluid. This air is preferably expunged by tilting the inflation device 10 upwards so that the connector 26 is higher in elevation than the remainder of the inflation device 10. The air or any other trapped gases will naturally rise towards the distal end 16 of the inflation device 10. The plunger assembly 30 is then advanced by distal advancement of the actuator 32 until the intermediate detent 44 is engaged. At this point, the inflation device is fully prepped with a desired volume of fluid, and ready to be connected to the balloon catheter 104 via the connector 26.

As described above, the dilation balloon 100 is inflated by advancing the plunger assembly 30 distally into the bore 18 of the syringe body 12. The pressure shut-off valve 50 responds to increasing pressure within the syringe body 12 by closing the fluid flow path A (illustrated in FIG. 5) to the balloon catheter 104 at a pre-prescribed or threshold pressure. Once the shut-off valve 50 is closed, higher pressures imparted to the fluid contained within the syringe body 12 are not transferred to the balloon catheter 104. Therefore, the pressure in the balloon catheter 104 will remain at a relatively constant pre-prescribed pressure and no higher.

To deflate the dilation balloon 100, the plunger assembly 30 is fully withdrawn proximally by proximal retraction of the actuator 32 until the distal detent 46 is engaged with the projection 92. The distal detent 46 serves to keep the plunger assembly 30 in this position and holds the partial vacuum pressure that has been established within the bore 18. This condition is maintained even if the user removes his or her hands from the actuator 32 or even if the entire the inflation device 10 is let go. As pressure in the bore 18 of the syringe body 12 is reduced by withdrawal of the plunger assembly 30, the pressure shut-off valve 50 is re-opened, allowing for deflation of the dilation balloon 100 as the plunger assembly 30 is further withdrawn. Upon fully withdrawing the plunger assembly 30, the balloon catheter 104 is exposed to partial vacuum pressure.

The desired maximum pressure that the dilation balloon 100 is exposed to can be designed into the shut-off valve 50 by varying one or more variables of the components making the shut-off valve 50. For example, a "stiffer" compression spring 66 (i.e., a higher spring constant) will result in a higher pressure required to actuate the shut-off valve 50. Alternatively, design variables associated with the amount of travel of the moveable piston 68 (shut-off "activation") can be considered. For a given compression spring 66, a shorter vs. longer distance from the "neutral" position (e.g., FIG. 5) to a "stopped" position (FIG. 6B) determined by the position of the distal stop 64 will alter the pressure required to activate the shut-off valve 50. For example, if the stop 64 is positioned (and associated variables such as position of the outlet 84 of the bypass lumen 82 and the aperture 86 are positioned) to effectively shorten the amount of compression required to close the shut-off valve 50, the resultant "activation pressure" required for actuating the shut-off valve 50 will be lower. The diameter of the moveable piston 68 (and associated components such as the o-rings 70, 72, 74 and bypass lumen 82) will also impact the pressure at which the shut-off valve 50 interrupts fluid communication.

In one embodiment, the pressure shut-off valve 50 is configured to shut off at 12 atmospheres of pressure. In this embodiment, the compression spring 66 has an elastic constant of 10 lb/in, such that when it is compressed to the point where the distal stop 64 is engaged 0.65 inches, a force of 7.3 lbs is required. The outer diameter of the moveable piston 68 and o-rings 70, 72, 74 are 6.1 mm. The bore 18 is preferably about 6.35 mm in diameter and 6.35 cm in length when the plunger assembly 30 is fully withdrawn (at full vacuum), which results in a relatively small volume and overall size when compared to prior art inflation devices.

As best seen in FIG. 4, the connector 26 may be integrally formed with a housing 29 that extends proximally and is mounted coaxially around the shut-off valve 50. This housing 29 is then secured to the syringe body 12. While numerous suitable methods may be employed, such as adhesive or solvent bonding, or ultrasonic welding, a preferred method is to "spin weld" the two components together. The housing 29 and the syringe body 12 are dry fitted together and then spun relative to each other to generate friction. This friction melts some of each material, forming a strong hermetic weld between the two components. In a likewise fashion, the projection 92 can be secured to the syringe body 12.

In one embodiment of the inflation device 10, there is no separate pressure gauge as is commonly found using prior art balloon catheter inflation devices. As a result, there is no "dead space" air volume. The inflation device 10 can therefore be "primed" with fluid with near totality. With little or no air in the inflation device 10, the volume of the syringe body 12 and the priming volume can be relatively small and still provide an adequate vacuum pressure to deflate the dilation balloon 100. In a preferred embodiment, the priming volume within the bore 18 of the syringe body 12 is 1.75 mL. In such an embodiment, one or more small indicators 94 (best illustrated in FIGS. 1, 2, 4, 5, 6A, 6B, 8 and 10-12) can be incorporated into the syringe body 12 to visibly observe the movement of the movable piston 68. Such indicators 94 can be positioned to correspond to the position of a location on the movable piston 68, e.g. the distal o-ring 70 at varying pressures to serve as a simple pressure gauge.

The relatively small size of the inflation device 10, coupled with the ability to be operated with one hand provides for an inflation apparatus that can be "directly connected" to the balloon catheter 104. Preferred balloon catheters 104 that may be used with the inflation device 10 described herein are described in U.S. patent application Ser. Nos. 11/379,691 and 11/623,740, which are incorporated by reference herein. As such, it is contemplated that a dilation system including the balloon catheter 104 and the inflation device 10 can be used by a single operator or, alternately, can be used more traditionally with two or more operators.

Figure 10:
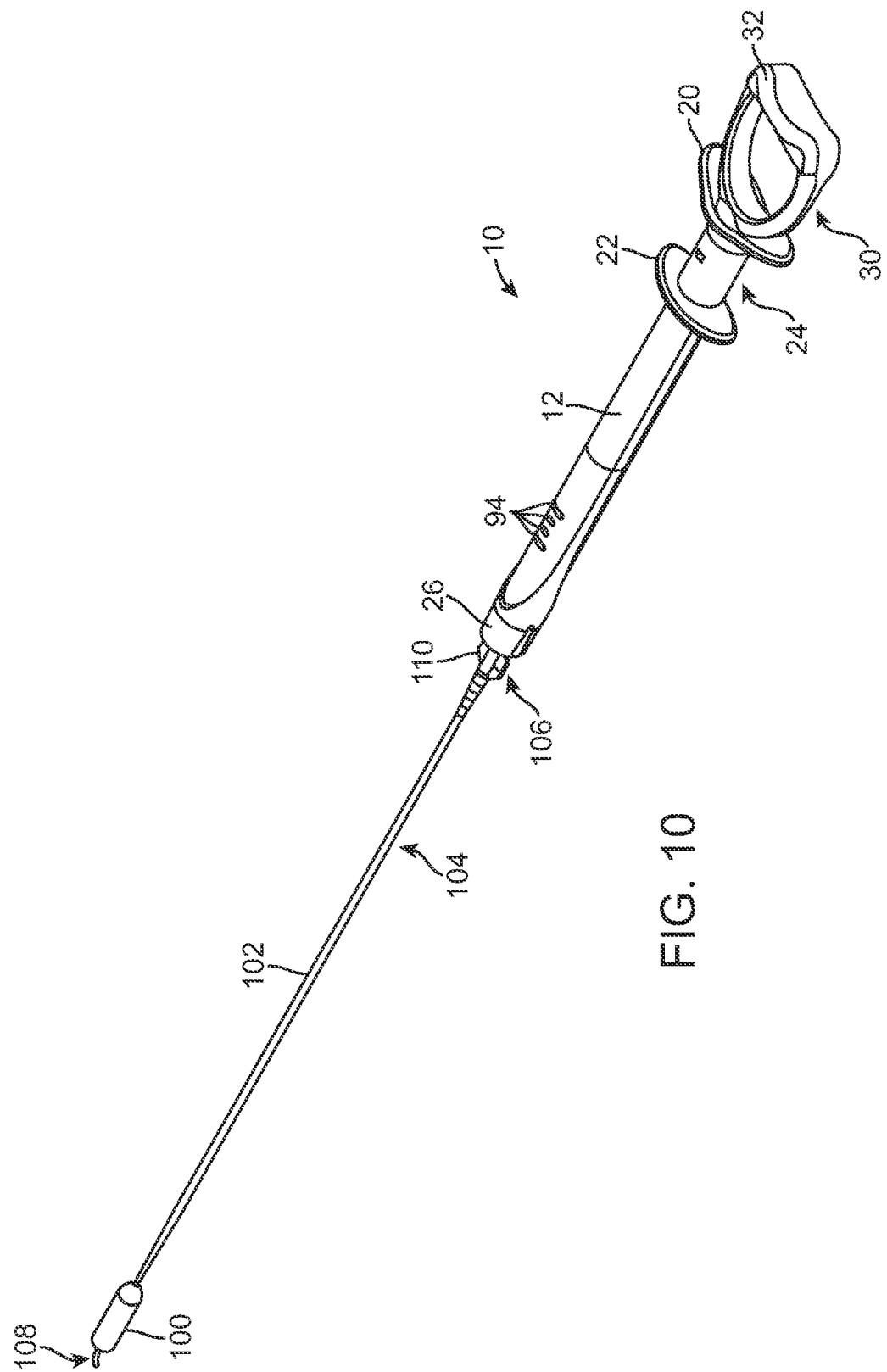
FIG. 10 is a perspective view of an inflation device coupled to a balloon catheter via a connector such as, for instance, a Luer connector. The balloon is illustrated in an inflated state as the plunger assembly has been advanced distally within the syringe bore.

FIG. 10 illustrates the inflation device 10 coupled to a balloon catheter 104. The balloon catheter 104 generally includes an elongate member 102 that has a proximal end 106 and a distal end 108. A dilation balloon 100 is disposed on or near the distal end 108 of the elongate member 102 and the interior portion of the dilation balloon 100 is fluidically coupled to a lumen (not shown) that extends the length of the elongate member 102. This lumen carries the fluid (e.g., saline) that is delivered via the inflation device 10 when the balloon catheter 104 is connected. As seen in FIG. 10, the proximal end 106 of the elongate member 102 terminates in a connector 110 that is configured to connect to the connector 26 disposed at the distal end 16 of the inflation device 10. The connector 100 may include a mating Luer connector to connect with the one illustrated in FIG. 10.

Figure 11:
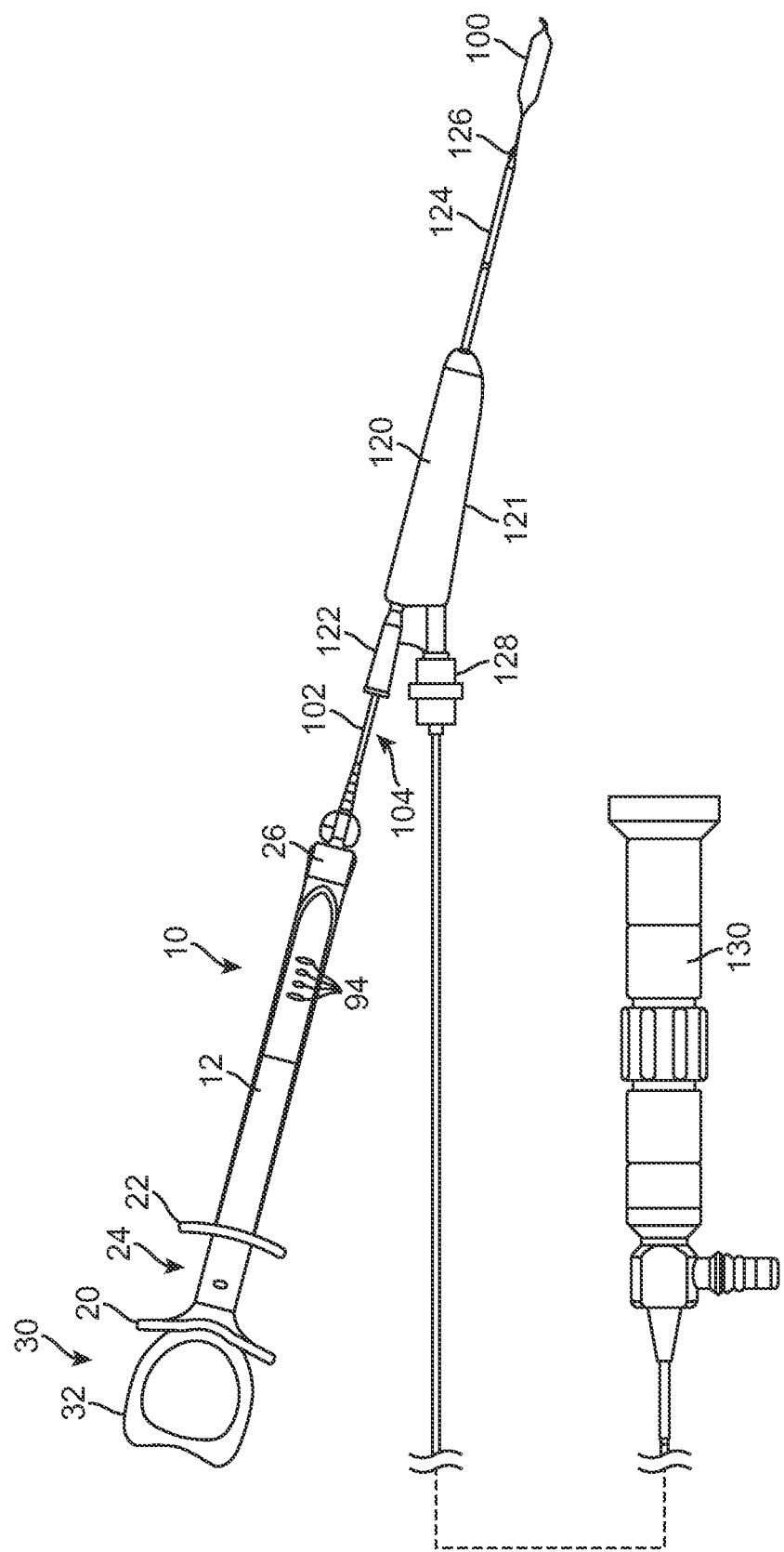
FIG. 11 illustrates an inflation device coupled to a balloon catheter that is situated within a cannula. The cannula is a dual-lumen cannula that includes a first port or opening for insertion of the balloon catheter. A second port or opening in the cannula communicates with a secondary lumen that is sized to receive a visualization device such as an endoscope. The endoscope is illustrated as being disposed in the cannula.

FIG. 11 illustrates the inflation device 10 that is coupled to a balloon catheter 104 that is disposed within a cannula 120. The cannula 120 may include a handle portion 121 that is configured to be grabbed or otherwise manipulated by the user. The cannula 120 includes a first inlet port 122 that is configured to receive a balloon catheter 104. The inlet port 122 leads to a first lumen (not shown) that extends to an elongate portion 124 of the cannula 120 and terminates at a distal end 126. The balloon catheter 104 can thus be introduced (in a deflated state) into the first inlet port 122 and advanced distally through the cannula 120 to place the dilation balloon 100 distally with respect to the distal end 126 of the cannula 120. The cannula 120 also includes a second inlet port 128 that is configured to receive a visualization device 130. The visualization device 130 may include, for example, an endoscope. The second inlet port 128 leads to a second lumen (not shown) that also extends to the elongate portion 124 of the cannula 120. The visualization device 130 can be introduced into the second inlet port 128 and advanced distally through the cannula 120 to place a distal end of the visualization device 130 in a position to ascertain a forward-looking field of view (e.g., looking toward the dilation balloon 100). Alternatively, the visualization device 130 may already be incorporated into the cannula 120 such that distal advancement is not necessary. As explained below, the visualization device 130 is typically inserted into the cannula 120 prior to the insertion of the balloon catheter 104.

The elongate portion 124 of the cannula 120 may be dimensioned such that it can pass through an artificial opening formed into a sinus passageway of a patient. For example, an artificial opening may be formed in the canine fossa region of a subject using a tool or other implement such as those disclosed in U.S. patent application Ser. Nos. 11/379,691, 11/623,740, and 12/038,719 which are incorporated by reference herein. The artificial passageway that is formed in the canine fossa region may be cannulated with a sheath or separate cannula as explained herein. The sheath or separate cannula may then serve to create a working opening through which the elongate portion 124 of the cannula 120 may be introduced.

As one exemplary method of using the system, the balloon catheter 104 may then be guided under visualization to place a deflated dilation balloon 100 across a natural ostium such as the maxillary sinus ostium. Other ostia beyond the maxillary sinus ostium may also be treated in this same fashion. The inflation device 10 as described in detail herein may then be used to dilate the dilation balloon 100 which is positioned with the natural ostium. This procedure opens or reduces the degree of constriction of the natural ostium and reduces patient symptoms associated with sinusitis.

FIG. 12 illustrates a balloon dilation catheter 104 placed across the natural ostium of the maxillary sinus 140. The dilation balloon 100 is illustrated in a dilated state, after the inflation device 10 has been actuated by distal advancement of the plunger assembly 30 within the syringe body 12. FIG. 12 further illustrates the visualization device 130 in the form of an endoscope being located in the second inlet port 128. A visualization field 142 extends from the distal end of the endoscope 130 and provides the user with a view of the operative working area using the eyepiece 144 and/or a camera 146 connected to the endoscope 130. The operative working area may, for example, be displayed on a monitor or similar device (not shown) for easy viewing during the procedure.

FIG. 12 illustrates the cannula 120 being positioned in the maxillary sinus 140 via an artificial opening created in the canine fossa region of the patient. Also, the elongate portion 124 of the cannula 120 is illustrated as being positioned within an access sheath 150 that includes optional cutting surfaces 152. As explained in U.S. patent application Ser. No. 12/038,719, the cutting surfaces 152 create longitudinally-oriented cutting surfaces at the outer perimeter of the distal tubular member and permit the user to ream or "side-cut" the artificial passageway to re-orient the system after initial access is made to the sinus cavity.

Figure 13:
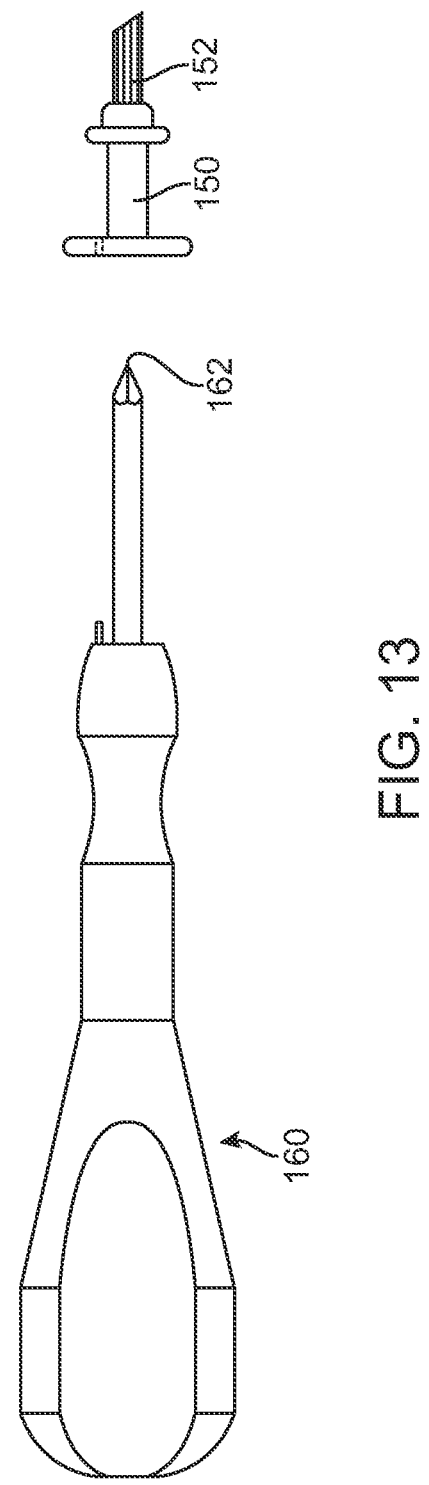
FIG. 13 illustrates an access tool and access sheath used to access the maxillary sinus of a patient via the canine fossa.

FIG. 13 illustrates the access tool 160 along with the access sheath 150. The access tool 160 (e.g., trocar) includes a cutting or penetrating tip 162 that is used to form the artificial passageway in the canine fossa. When forming the artificial passageway in the canine fossa, the access sheath 150 is loaded onto the shaft of the access tool 160. After the tissue has been penetrated, the access tool 160 can be removed proximally, leaving the access sheath 150 in place.

For a typical procedure, the various components of the system are provided as part of a sterile kit. For example, the kit may be packaged or boxed and include inflation device 10, the balloon catheter 104, the catheter 120, access tool 160, and access sheath 150. The visualization device 130 is typically not part of the kit. The individual items from the kit may then be removed in advance of use. Some users may prefer to withdraw the balloon catheter 104 and prepare the balloon catheter 104 using a separate syringe device.

Alternatively, the balloon catheter 104 is primed using the inflation device 10 described herein. In particular, the end of the distal end 16 of the inflation device 10 is placed in saline or other inflation fluid. The plunger assembly 30 is then fully withdrawn in the proximal direction by proximal movement of the actuator 32 until the distal detent 46 engages with the projection 92. Any entrained air is expunged by elevating the distal end 16 of the inflation device 10 and then advancing the actuator 32 until the intermediate detent 44 is engaged with the projection 92. The inflation device 10 may be connected to the balloon catheter 104 via the connector 26 and set aside until needed later in the procedure.

Next, the physician will then form the artificial passageway in the canine fossa of the patient using the access tool 160 and access sheath 150. The access sheath 150 is placed on the access tool 160 and a puncture is formed in the canine fossa region. The access tool 160 is then withdrawn proximally leaving in place the access sheath 150. Optionally, the cutting surfaces 152 of the access sheath 150 may be used to ream out the artificial opening and reposition to the access sheath 150 to the desired orientation. The visualization device 130 (e.g., endoscope) is advanced into the cannula 120 and locked into place. Alternatively, the visualization device 130 may have already been advanced or otherwise secured to the cannula 120. The cannula 120 and visualization device 130 are then advanced through the access sheath 150 into the maxillary sinus cavity 140 (or other sinus cavity). This advancement is typically done under visualization using a camera 146 or the like that outputs the image onto a display where the physician may view the visual field 142 in real time.

In the case where the natural sinus ostium of the maxillary sinus 140 is to be treated, the physician will locate the ostium using the visualization device 130. After the correct orientation is made of the cannula 120, the physician then advances the balloon catheter 104 (with the dilation balloon 100 in the deflated state) through the inlet port 122 of the cannula 120. The balloon catheter 104 is advanced to traverse the natural sinus ostium of the maxillary sinus 140 with the dilation balloon 100. Once into position, the operator can then depress the actuator 32 and advance the shaft 34 until the piston 68 moves distally to engage the mount 64 and the proximal detent 46 engages with the projection 92. Typically, the piston 68 reaches the shut-off position prior to the proximal detent 46 reaching the projection 92. At this point, the dilation balloon 100 is inflated with the fluid and thus expands within the natural ostium. This is illustrated in FIG. 12. Some physicians may deflate the dilation balloon 100 and then re-inflate the dilation balloon 100 one or more times to ensure that proper dilation was accomplished.

Once treatment is complete, the dilation balloon 100 is deflated and the balloon catheter 104 is withdrawn proximally from the cannula 120. The cannula 120 and the visualization device 130 are then removed from the access sheath 150. Finally, the access sheath 150 is removed from the artificially created opening.

While an entire procedure is described above in connection with approaching a natural sinus ostium via the canine fossa, the tools described above, particularly the balloon catheter 104 and inflation device 10 could also be used in other procedures, for example for dilating a natural sinus ostium such as the maxillary sinus ostium or a frontal sinus ostium or a sphenoid sinus ostium via a transnasal approach through the nostril.

While embodiments of the present invention have been shown and described, various modifications may be made without departing from the scope of the present invention. The invention, therefore, should not be limited, except to the following claims, and their equivalents.

What is claimed is:

1. A method of using an inflation device comprising:
    securing an inflation device to a proximal connector of a balloon dilation catheter comprising an elongate member having a dilation balloon at one end and the proximal connector at an opposing end, the inflation device comprising:
        a syringe body having proximal end and a distal end and a bore contained therein, the bore configured to hold a fluid therein;
        a plunger assembly configured for slidable movement within the syringe bore, the plunger assembly comprising a shaft having a sealing member configured to form a fluid tight seal with the syringe body;
        a distal connector disposed at the distal end of the inflation device, the distal connector containing an aperture configured for passage of fluid, wherein the distal connector is configured to mate with the proximal connector of the balloon dilation catheter;
        a fluid bypass channel disposed in the distal end of the syringe body and fluidically coupled to the aperture of the distal connector; and
        a shut-off valve coaxially disposed within the bore of the syringe body comprising a spring-biased moveable piston having a bypass lumen contained therein, wherein the bypass lumen forms a fluid path between the bore and the fluid bypass channel in the syringe body when the pressure of the fluid is below a threshold value and wherein the fluid path between the bore and the fluid bypass channel is interrupted when the pressure of the fluid is above the threshold value, and wherein the fluid bypass channel is formed between an exterior surface of the shut-off valve and an interior surface of the bore of the syringe;
    advancing the balloon dilation catheter into a body lumen; and
    advancing the plunger assembly in the bore so as to inflate the dilation balloon.

2. The method of claim 1, wherein the body lumen comprises a sinus passageway.

3. The method of claim 2, wherein the balloon dilation catheter is advanced to the sinus passageway transnasally.

4. The method of claim 2, wherein the balloon dilation catheter is advanced to the sinus passageway via an artificial opening.

5. The method of claim 2, wherein the sinus passageway comprises a natural ostium.

6. The method of claim 1, wherein the balloon dilation catheter is advanced through a separate catheter.

7. The method of claim 1, wherein the volume of the bore is about 1.75 mL.

8. The method of claim 1, wherein the assembled balloon dilation catheter and the inflation device does not include a separate pressure gauge.

9. The method of claim 1, further comprising stopping advancement of the plunger assembly when the sealing member reaches one or more indicators disposed on a surface of the syringe body.

10. The method of claim 9, further comprising advancing the plunger assembly in the bore so as re-inflate the dilation balloon.

11. The method of claim 1, further comprising retracting the plunger assembly in the bore so as to deflate the dilation balloon.

12. The method of claim 1, wherein the proximal connector comprises a Luer connector.

13. The method of claim 1, wherein the balloon dilation catheter is advanced under visualization.

14. The method of claim 1, wherein the threshold comprises about 12 atmospheres of pressure.

* * * * *